United States Patent
Yamaguchi

(10) Patent No.: US 10,667,495 B2
(45) Date of Patent: Jun. 2, 2020

(54) SOUND COLLECTOR, ANIMAL EMOTION ESTIMATION DEVICE, AND ANIMAL EMOTION ESTIMATION METHOD

(71) Applicant: Langualess Inc., Tokyo (JP)

(72) Inventor: Joji Yamaguchi, Nagano (JP)

(73) Assignee: Langualess Inc., Tokyo (JP)

( * ) Notice: Subject to any disclaimer, the term of this patent is extended or adjusted under 35 U.S.C. 154(b) by 176 days.

(21) Appl. No.: 15/735,242

(22) PCT Filed: Jun. 13, 2016

(86) PCT No.: PCT/JP2016/067574
§ 371 (c)(1),
(2) Date: Feb. 9, 2018

(87) PCT Pub. No.: WO2016/199938
PCT Pub. Date: Dec. 15, 2016

(65) Prior Publication Data
US 2018/0177158 A1    Jun. 28, 2018

(30) Foreign Application Priority Data

Jun. 12, 2015   (JP) ................................. 2015-119629

(51) Int. Cl.
```
A01K 27/00      (2006.01)
A61B 5/00       (2006.01)
A61B 5/024      (2006.01)
A61B 5/16       (2006.01)
A01K 29/00      (2006.01)
A01K 11/00      (2006.01)
A61B 7/04       (2006.01)
H04R 1/46       (2006.01)
```
(52) U.S. Cl.
CPC ............ *A01K 27/006* (2013.01); *A01K 11/00* (2013.01); *A01K 29/00* (2013.01); *A01K 29/005* (2013.01);

(Continued)

(58) Field of Classification Search
CPC ...... A01K 27/006; A01K 29/00; A01K 11/00; A01K 29/005; H04R 1/46; A61B 7/04;
(Continued)

(56) References Cited

U.S. PATENT DOCUMENTS

2008/0310663 A1*  12/2008  Shirasaka ............ H04R 19/016
                                                    381/355
2013/0207806 A1*   8/2013  Lehmann ............. H04B 1/3838
                                                    340/600

(Continued)

FOREIGN PATENT DOCUMENTS

JP       51-084183 A     7/1976
JP       56-075975 A     6/1981
(Continued)

OTHER PUBLICATIONS

Spotlight, http://spotlight-media.jp/article/94759895630353717 (Year: 2014).*

(Continued)

*Primary Examiner* — Catherine M Voorhees
(74) *Attorney, Agent, or Firm* — DLA Piper LLP (US)

(57) ABSTRACT

An animal emotion estimation device includes: a sound collector configured by an elastic member having a recess, a sound concentrating microphone provided on the bottom portion of the recess, and an impact absorber covering the entire of the elastic member and the sound concentrating microphone; a harness to mount the sound collector on an animal; a converter that filters and converts the sound collected through the sound collector into a heart rate signal; an estimation portion that estimates the emotion of the animal based on the heart rate signal; and an output unit that supplies information showing the estimation estimated by the estimation portion.

19 Claims, 16 Drawing Sheets

(52) U.S. Cl.
CPC .......... *A61B 5/02438* (2013.01); *A61B 5/165* (2013.01); *A61B 5/6823* (2013.01); *A61B 5/6831* (2013.01); *A61B 5/742* (2013.01); *A61B 7/04* (2013.01); *H04R 1/46* (2013.01); *A61B 5/7257* (2013.01); *A61B 2503/40* (2013.01)

(58) Field of Classification Search
CPC . A61B 5/165; A61B 2503/40; A61B 5/02438; A61B 5/6831; A61B 5/7257; A61B 5/6823; A61B 5/742
See application file for complete search history.

(56) References Cited

U.S. PATENT DOCUMENTS

2014/0318699 A1* 10/2014 Longinotti-Buitoni ...................... A61B 5/0002
156/247
2015/0104027 A1* 4/2015 Mulumudi ............... H04R 1/46
381/67

FOREIGN PATENT DOCUMENTS

| JP | 60-25294 A | 2/1985 |
| JP | 2000-316825 A | 11/2000 |
| JP | 2004-021243 A | 1/2004 |
| JP | 2006-017753 A | 1/2006 |
| JP | 2010-187631 A | 9/2010 |
| JP | 2014-230538 A | 12/2014 |
| JP | 2014230538 A * | 12/2014 |

OTHER PUBLICATIONS

Notice of Reasons for Refusal dated Feb. 26, 2019 of counterpart Japanese Application No. 2017-523741 along with an English translation.
Notice of Reasons for Refusal dated Apr. 23, 2019, of counterpart Japanese Application No. 2017-523741 along with an English translation.
Spotlight, http://spotlight-media.jp/article/94759895630353717, 2014.

* cited by examiner

FIG. 6

| ESTIMATED STATE OF ANIMAL | DISPLAY INFORMATION |
|---|---|
| DROWSINESS: YES<br>DEGREE OF STRESS:<br>DEGREE OF INTEREST: | 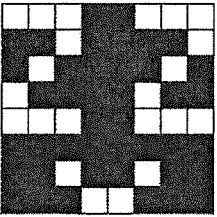 |
| DROWSINESS: NO<br>DEGREE OF STRESS: HIGH<br>DEGREE OF INTEREST: HIGH | 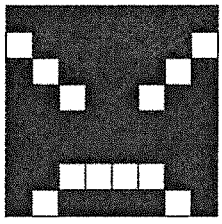 |
| DROWSINESS: NO<br>DEGREE OF STRESS: HIGH<br>DEGREE OF INTEREST: LOW | 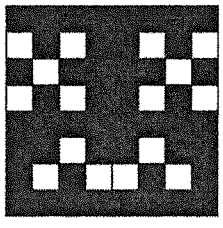 |
| DROWSINESS: NO<br>DEGREE OF STRESS: LOW<br>DEGREE OF INTEREST: HIGH | 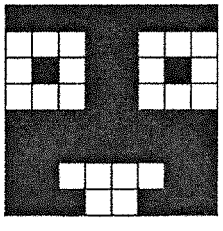 |
| DROWSINESS: NO<br>DEGREE OF STRESS: LOW<br>DEGREE OF INTEREST: LOW | 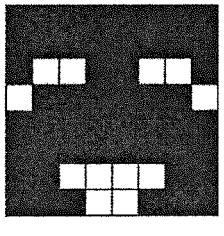 |

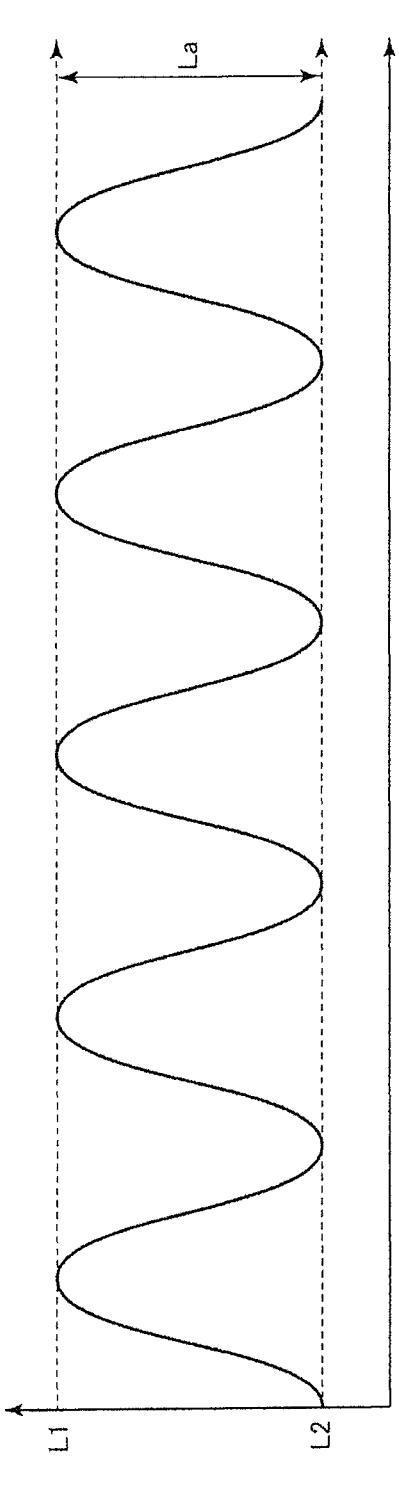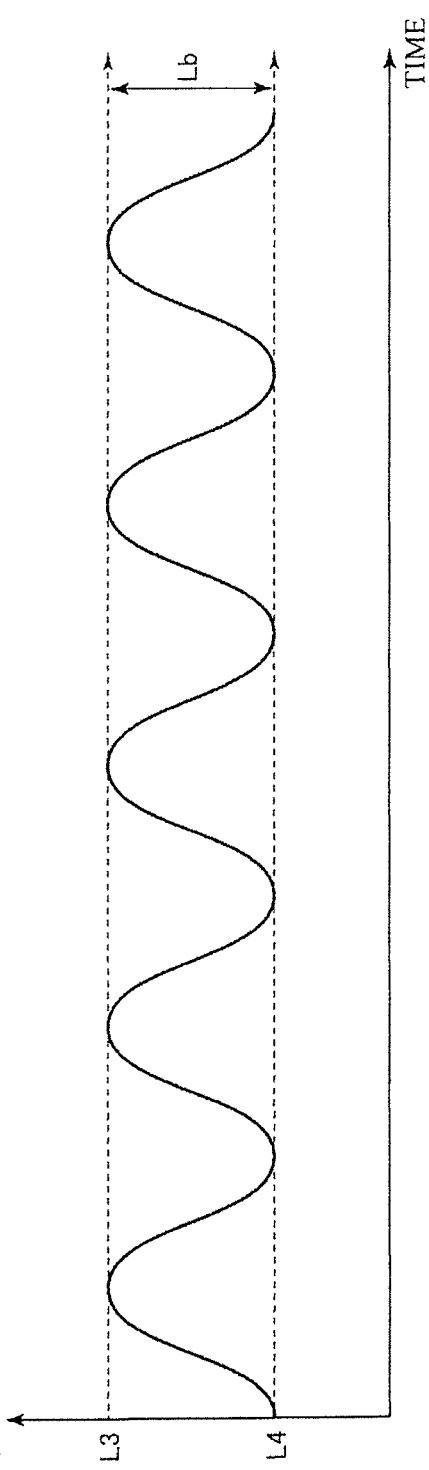

FIG. 14

| BASIC COLOR | HEART RATE (TIMES/MIN) |
|---|---|
| BLUE | ~65 |
| GREEN | 66~70 |
| YELLOW | 71~75 |
| RED | 76~ |

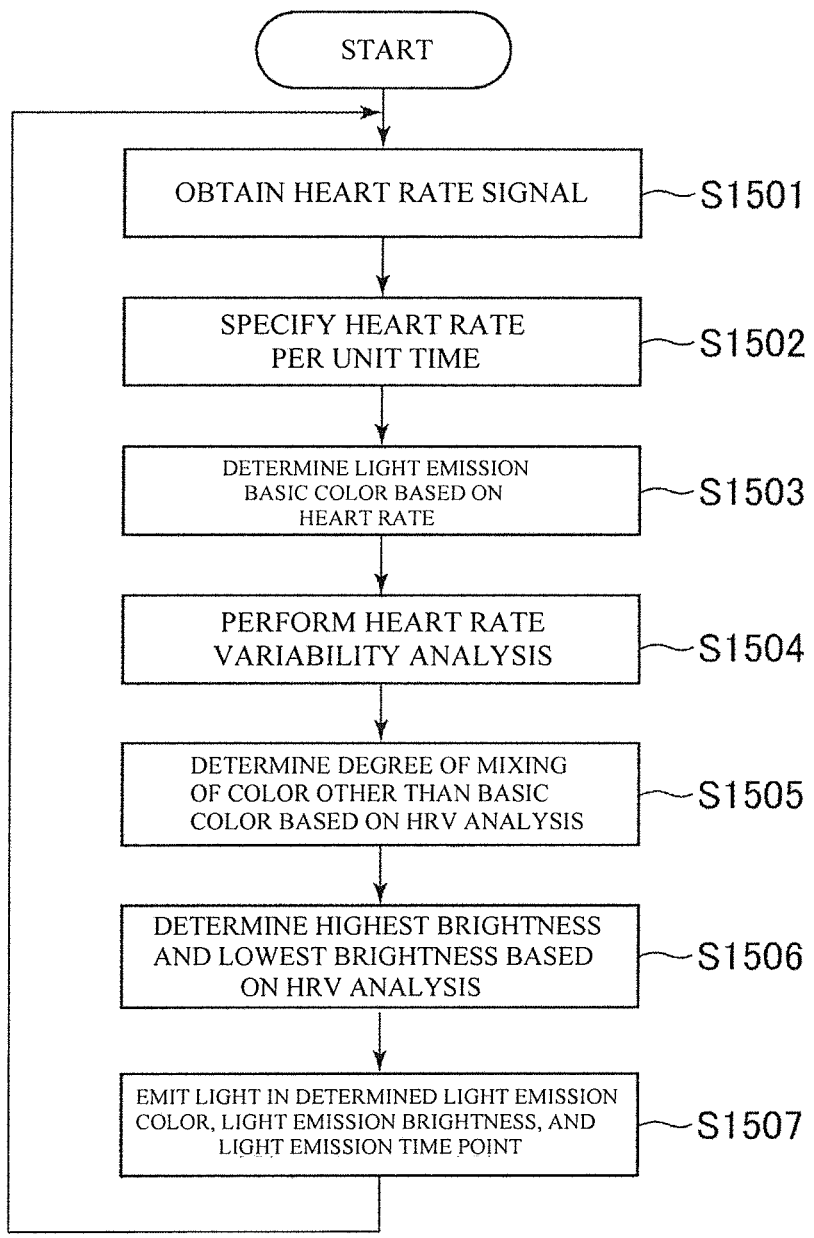

… (1)

SOUND COLLECTOR, ANIMAL EMOTION ESTIMATION DEVICE, AND ANIMAL EMOTION ESTIMATION METHOD

TECHNICAL FIELD

This disclosure relates to a device that estimates an emotion of an animal.

BACKGROUND

Conventionally, owners who keep various kinds of pets have troubles in more precisely understanding emotions of the breeding pets. They could communicate more smoothly and make friends with the pets with better understanding.

As shown in Japanese Unexamined Patent Application Publication No. 2010-187631 (JP 2010-187631 A), a device that estimates an emotion of a small animal has been developed. In the technique disclosed in JP 2010-187631 A, the device includes an electrode, a foot of a small animal is placed on the electrode, and a weak current flows therethrough to stimulate the foot to obtain a biological potential. The device then computes and displays the degree of relaxation and the degree of excitement based on the obtained biological potential.

However, in the device disclosed in JP 2010-187631 A, since the foot of the small animal needs to be placed on the electrode, it is hard to obtain the biological potential in the natural state of the small animal to estimate the emotion of the small animal in everyday life, and thus the device fails to satisfy the user's needs.

It could therefore be helpful to provide an animal emotion estimation device and a sound collector for use in the animal emotion estimation device, allowing the user to recognize the emotion of the animal in general life.

SUMMARY

I thus provide:

A sound collector including: an elastic member having a recess; a sound concentrating microphone provided in a bottom portion of the recess; and an impact absorber covering the entire of the elastic member and the sound concentrating microphone.

An animal emotion estimation device including: the sound collector above, a harness for mounting the sound collector on an animal, a converter that filters and converts a sound collected through the sound collector into a heart rate signal, an estimation portion that estimates an emotion of the animal based on the heart rate signal, and an output unit that supplies information showing the emotion estimated by the estimation portion.

An animal emotion estimation method corresponds to an animal emotion estimation method of estimating an emotion of an animal by an animal emotion estimation device mounted on the animal, including the steps of: obtaining a sound signal including a heart sound of the animal; converting the obtained sound signal into a heart rate signal; estimating the emotion of the animal based on the heart rate signal; and supplying information showing the estimated emotion.

The animal emotion estimation device may be mounted on the animal so that the device estimates the emotion of the animal using the heart rate signal obtained based on the sound signal collected through the sound collector, and supplies the information showing the estimated emotion.

Accordingly, recognizing the emotion supplied by the animal emotion estimation device mounted on the animal allows the user to recognize the emotion of the animal at each time at a glance.

BRIEF DESCRIPTION OF THE DRAWINGS

Features, advantages, and technical and industrial significance of examples of the disclosure will be described below with reference to the accompanying drawings, in which like numerals denote like elements.

FIG. 6 is a conceptual data diagram illustrating a configuration example of a face image table.

FIG. 13A is a graph illustrating an example of a brightness difference of blinking intervals of LEDs according to the degree of concentration of the animal.

FIG. 13B is a graph illustrating an example of a brightness difference of blinking intervals of LEDs according to the degree of concentration of the animal.

FIG. 14 is a conceptual data diagram illustrating a data configuration example of a basic color determination table 1400 according to Example 2.

FIG. 15 is a flowchart illustrating the operations of the animal emotion estimation device 10 according to Example 2.

DETAILED DESCRIPTION

Example 1

An animal emotion estimation device according to an example will be described in details below with reference to the drawings.

Outline

Figure 1A:
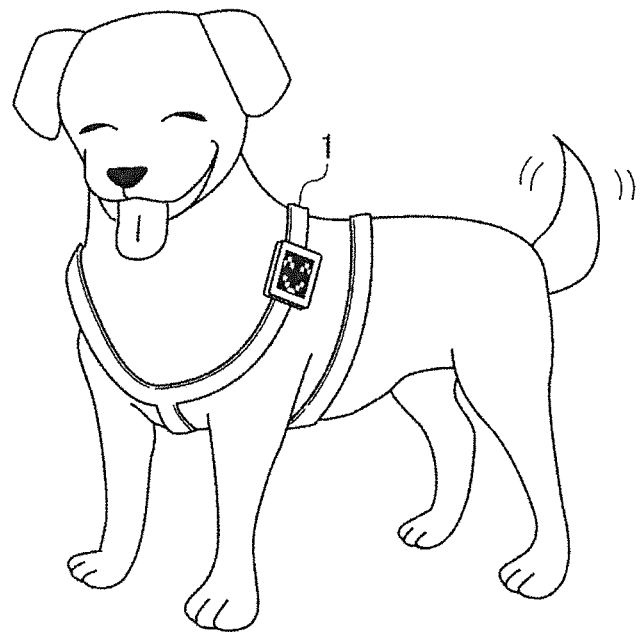
FIG. 1A is a diagram illustrating a state in which an animal emotion estimation device is mounted on an animal.

The animal emotion estimation device roughly estimates an emotion of an animal and presents the roughly estimated emotion showing what the animal is thinking about to a user such as an owner. As shown in FIG. 1A, the animal emotion estimation device 1 is mounted on the animal (dog in FIG. 1) for use. The animal emotion estimation device 1 collects the heartbeat sound of the animal on which the device 1 is mounted using a sensor (sound collector) 100 shown in FIG. 1B, and estimates the emotion of the animal based on the heart rate signal showing the obtained heartbeat sound. The animal emotion estimation device 1 then displays a face showing the emotion of the animal at each time on the output unit 200 provided in the animal emotion estimation device 1 shown in FIG. 1B. This allows the user to recognize what emotion the animal feels. The animal emotion estimation device 1 according to an example will be described in details below.

Configurations

Figure 1B:
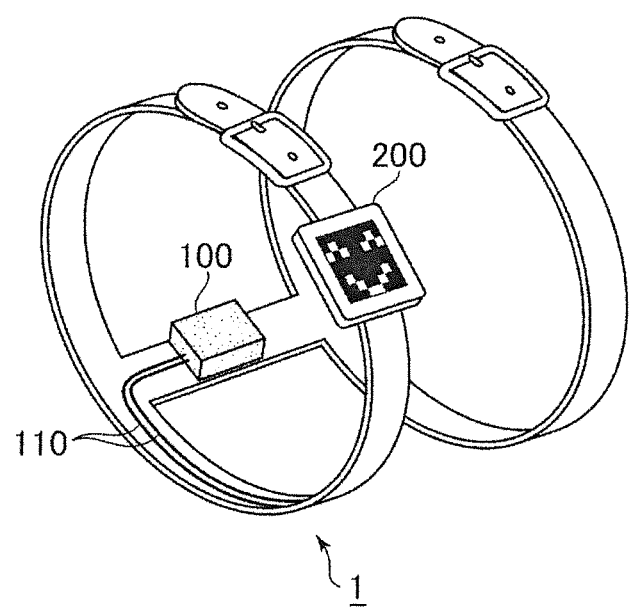
FIG. 1B is an outline drawing illustrating the animal emotion estimation device.

As shown in FIGS. 1A and 1B, the animal emotion estimation device 1 is configured to be mounted on the target animal, and includes a control device fixed onto a harness for the animal, which control device includes the sensor 100 and the output unit 200. Although FIG. 1 shows an example where the device 1 is mounted on the dog, the device 1 may be mounted on any animal other than the dog.

Figure 2A:
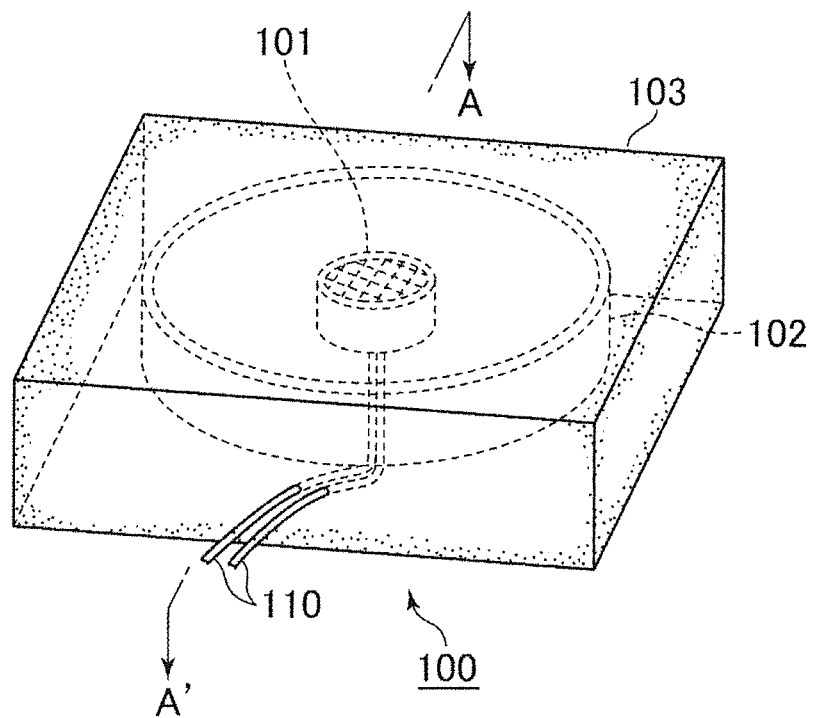
FIG. 2A is an outline drawing illustrating a sensor 100.
Figure 2B:
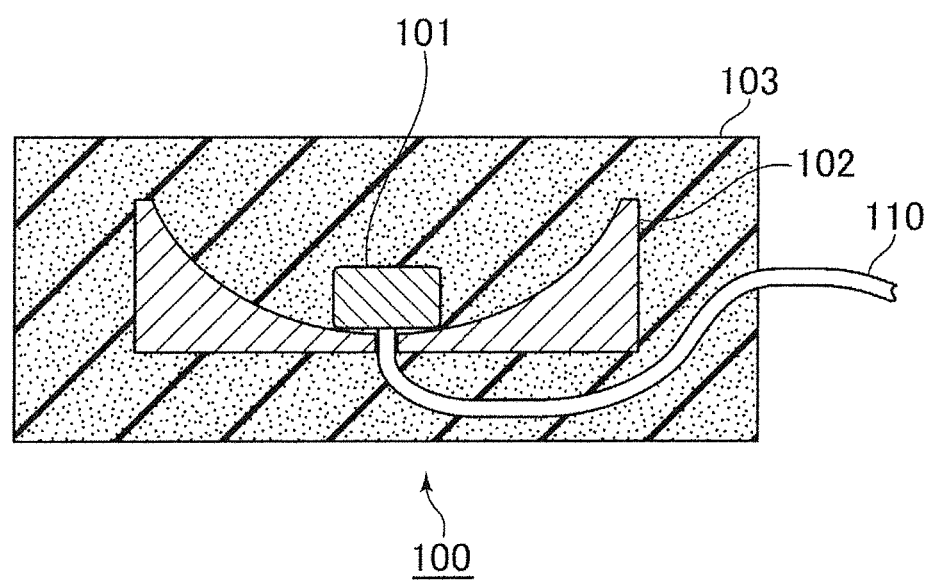
FIG. 2B is a cross sectional view illustrating the sensor 100 along line A-A'.

The sensor 100 is provided on an inner side of the animal emotion estimation device 1 such that the sensor 100 closely contacts the body surface of the animal on which the animal emotion estimation device 1 is mounted. This allows a microphone provided in the sensor 100 to obtain a sound signal in which the heartbeat sound is recorded. As shown in FIG. 1B, the sensor 100 is connected through a connecting wiring 110 to the output unit 200 such that the sound signal collected by the sensor 100 is transmitted therethrough. FIGS. 2A and 2B are diagrams illustrating the configuration of the sensor 100. FIG. 2A is a perspective view illustrating the sensor 100, and FIG. 2B is a cross sectional view of the sensor 100 in FIG. 2A along line A-A'.

As shown in FIG. 2A, the sensor 100 corresponds to a sound collector including a microphone 101 and a basal portion 102 that has a parabolic recess in a sponge 103 as an impact absorber. As shown in FIGS. 2A and 2B, the basal portion 102 is made of an elastic member such as a resin and has a parabolic (mortar-shaped, funnel-shaped) recess. Although the resin is used for the basal portion in consideration of weight reduction, it may be a harder material, and it is preferable that a material with high reflectance against sound waves be used. The microphone 101 is provided in the bottom portion of the recess such that the connecting wiring 110 is led out of the sponge 103.

The microphone 101 is provided on the bottom portion of the basal portion 102 to obtain a sound in the direction in which the microphone 101 is oriented, i.e., in the direction toward the animal, and the basal portion 102 reflects and absorbs the sound in the direction other than the direction toward the animal to limit the noise to be mixed.

Figure 3:
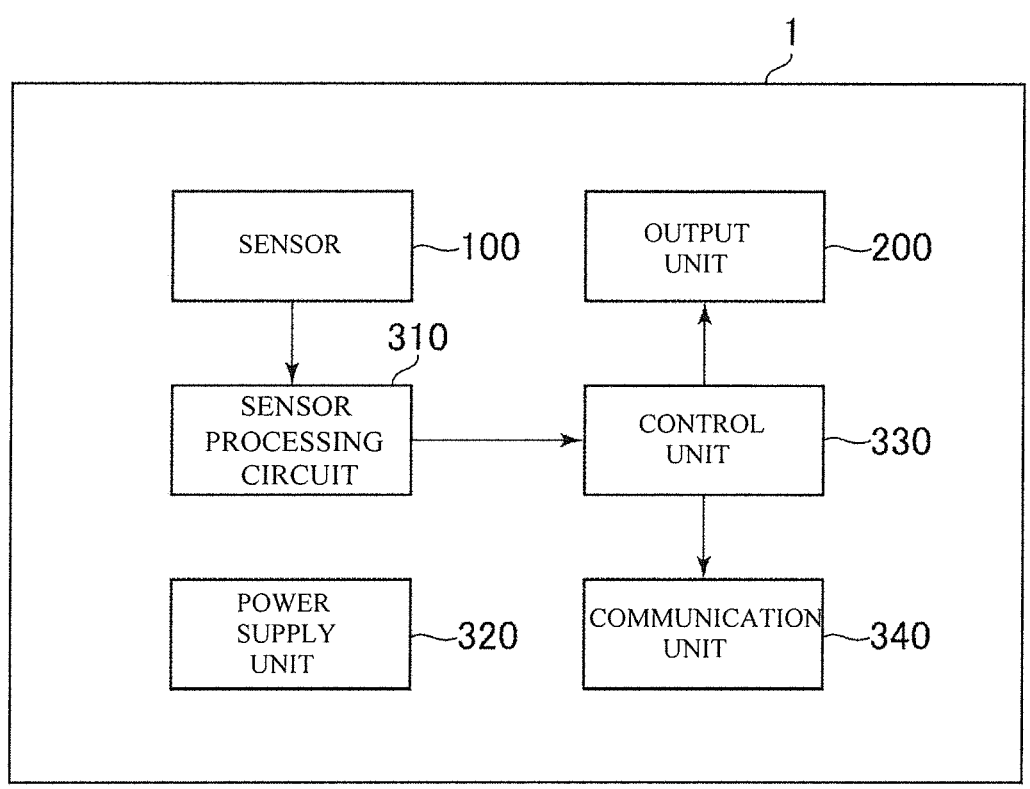
FIG. 3 is a block diagram illustrating a functional configuration of the animal emotion estimation device.

The sponge 103 is provided to cover the entirety of the microphone 101 and the basal portion 102 so that the sponge serves as a conductive member of the sound, and the sponge changes its shape as well to conform to the distortion of the skin caused by the movement of the animal, allowing the close contact state between the sensor 100 and the animal to be maintained. FIG. 3 is a functional block diagram illustrating the functional configuration of the animal emotion estimation device 1.

As shown in FIG. 3, the animal emotion estimation device 1 includes the sensor 100, the output unit 200, a sensor processing circuit 310, a power supply unit 320, a control unit 330, and a communication unit 340.

The sensor 100 obtains the ecological information of the animal on which the animal emotion estimation device 1 is mounted, and in this example the sensor 100 is embodied by a sound collector that obtains a sound. The sensor 100 transmits the obtained sound signal to a sensor processing circuit 310.

Figure 4:
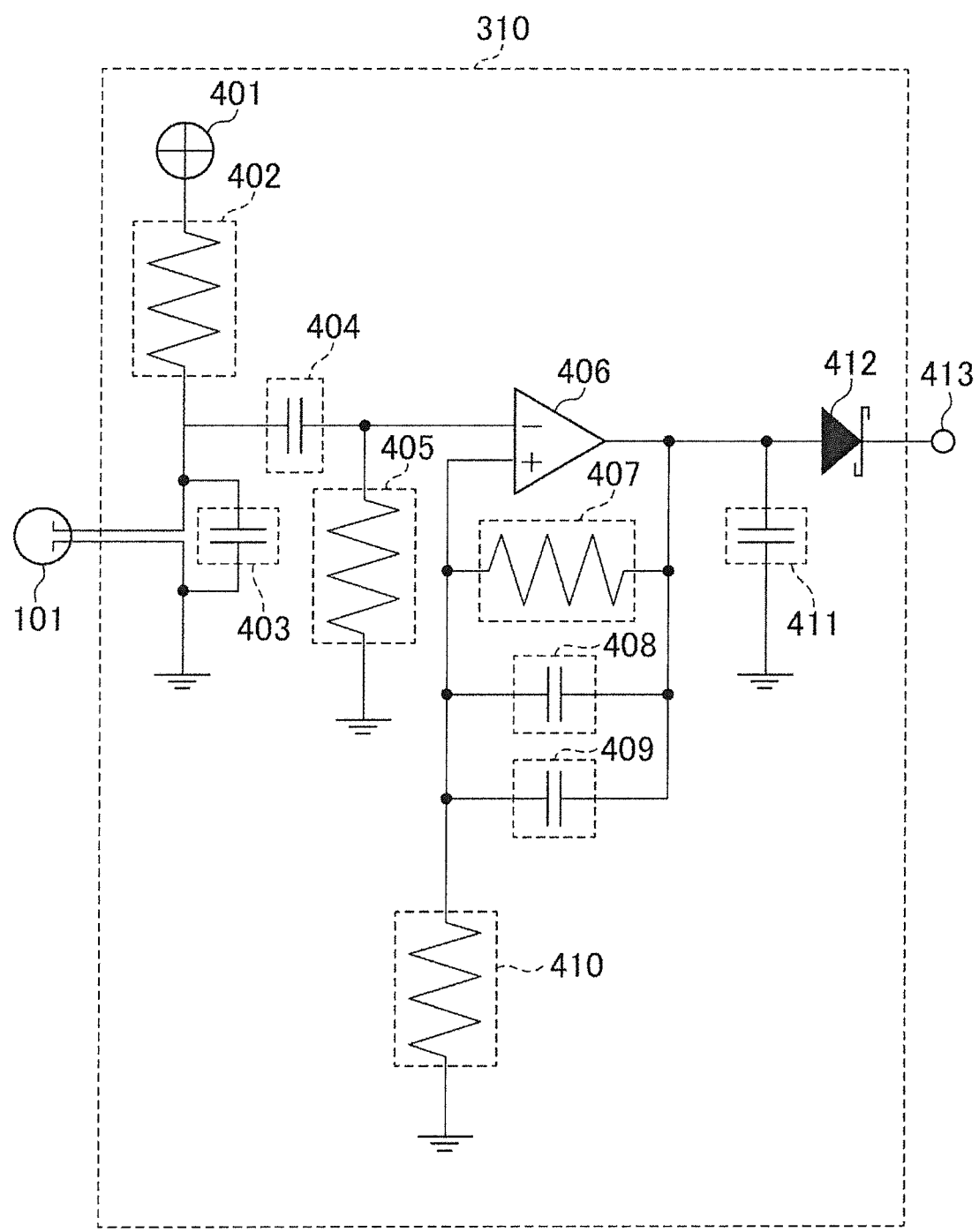
FIG. 4 is a circuit diagram illustrating a configuration of a sensor processing circuit.

The sensor processing circuit 310 corresponds to a circuit configured as shown in FIG. 4, and converts the sound signal into a heart rate signal and transmits the signal to a control unit 330. As for FIGS. 1A and 1B, the sensor processing circuit 310 is built in a portion of the device 1 where the output unit 200 is provided.

As shown in FIG. 4, the sensor processing circuit 310 includes a power input unit 401, a resistance 402, a capacitor 403, a capacitor 404, a resistance 405, an operational amplifier 406, a resistance 407, a capacitor 408, a capacitor 409, a resistance 410, a capacitor 411, and a Schottky barrier diode 412 that are connected.

The resistance 402 limits the power supplied from the power input unit 401.

The resistance 402 is assumed to be 100Ω to 10 kΩ here.

The capacitor 403 is set to 1 μF to 100 μF here, and is a noise filter that removes the noise of the sound signal supplied from the sensor 100.

For the sensor 100, an electret condenser microphone (ECM) is used here.

The capacitor 403 removes noise from the sound signal, and then the capacitor 404 and the resistance 405 remove a low frequency component from the sound signal from which the noise has been removed. That is, the capacitor 403 and the resistance 405 serve as a high-pass filter. In this case, the capacitor 403 is set to 0.1 μF to 10 μF, and the resistance 405 is set to 100Ω to 10 kΩ.

The operational amplifier 406 then amplifies the sound signal from which the low frequency component has been removed.

The amplification factor of the operational amplifier is determined based on the resistance 407 and the resistance 410. The resistance 407 is set to 20 kΩ to 200 kΩ, and the resistance 410 is set to 10Ω to 100Ω. This allows the operational amplifier 406 to have an amplification factor of about 2,000 to 20,000 times.

The capacitor 408 and capacitor 409 with total of 10 μF to 100 μF are used, which serve as a filter for the operational amplifier.

The capacitor 411 with 1 μF to 100 μF is used, which serves as a low pass filter.

The Schottky barrier diode 412 supplies the filtered heart rate signal to the output unit 413 and limits the reverse flow of the signal from the output unit 413 (control unit 330).

Returning to FIG. 4, the power supply unit 320 supplies power to each portion of the animal emotion estimation device 1. The power supply unit 320 may be a lithium ion battery, an alkaline battery, and a manganese dioxide battery, for example.

Figure 5A:
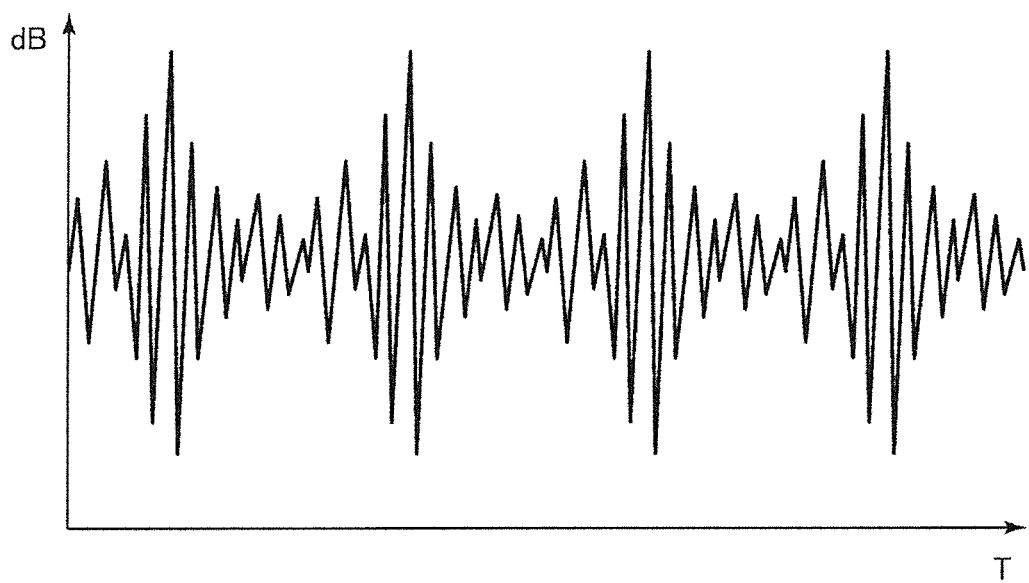
FIG. 5A is a wave form chart illustrating an example of the collected sound signal.
Figure 5B:
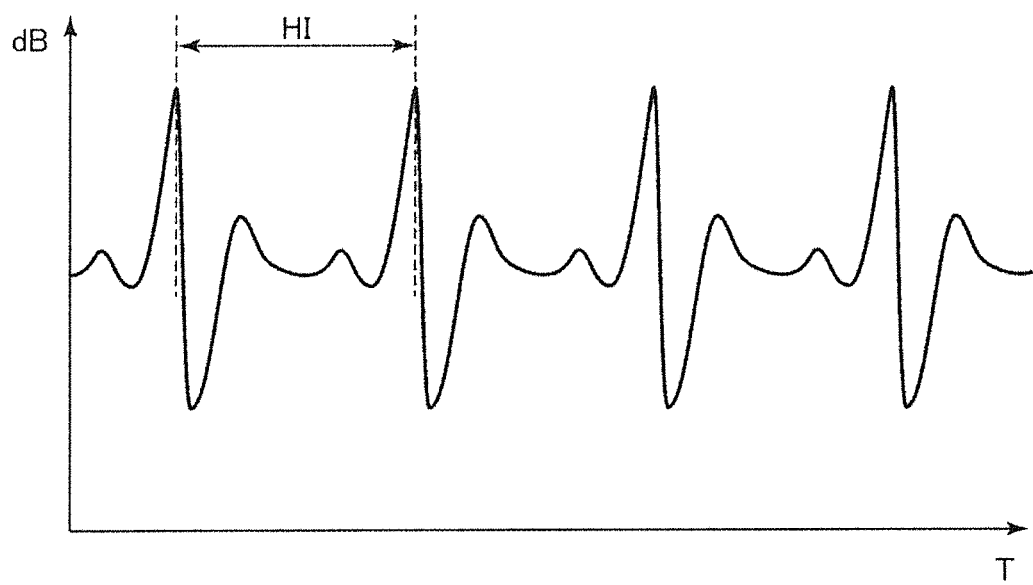
FIG. 5B is a wave form chart illustrating an example of a heart rate signal filtered by the sensor processing circuit.

The operations of the sensor processing circuit 310 convert a sound signal mixed with a noise as shown in FIG. 5A into a heart rate signal as shown in FIG. 5B.

The control unit 330 estimates the emotion of the animal based on the heart rate signal transmitted from the sensor processing circuit 310. The control unit 330 then transmits a face image based on the estimated emotion of the animal to the output unit 200. The control unit also serves to transmit the face image based on the estimated emotion of the animal to the communication unit 340.

A method of estimating the emotion of the animal by the control unit 330 will be described below. The control unit 330 estimates the emotion of the animal by performing a heart rate variability analysis (HRV analysis) based on the heart rate signal transmitted from the sensor processing circuit 310.

The well-known HRV analysis includes a technique referred to as NN50. In the technique, the number of times (NN50) of the consecutive observations is counted where the difference in the R-R intervals of the R-R intervals (corresponding to the intervals between the pulsation and the pulsation, the section HI in FIG. 5B shows the R-R intervals) in a predetermined number of samples (corresponding to a heart rate during a predetermined period of time (for example, 1 minute), e.g., 60) is greater than or equal to 50 ms. The technique corresponds to a method of determining whether the sympathetic nerve is active based on the value of pNN50 obtained by dividing the NN50 by the number of samples for the R-R interval. If the pNN50 is low, it is determined that the sympathetic nerve is active (feeling stress). However, since the value of 50 ms here applies to human beings, the value fails to be applied to an animal as it is.

Accordingly, the control unit 330 of the animal emotion estimation device 1 first converts the time of 50 ms for a human being into the time of X ms for an animal.

The time of 50 ms used for the NN50 analysis of a general human being is computed based on the average heart rate of a human being in a stable state without arrhythmia. In consideration of a fact that the generally known human heartbeat is 80 beats per minute (bpm), the average R-R interval of a human being is 750 ms (60×1000÷80=750). The 50 ms corresponds to 6.7% of the average R-R interval.

Accordingly, when the average R-R interval of the animal is set to 1000 ms, the time of X ms that is a time of pNNX of the animal is computed as X=1000×0.067=67 ms. Accordingly, the control unit 330 computes the average R-R interval from the obtained heart rate signal, and multiplies the average R-R interval by the ratio 6.7% to obtain the time of X ms for an animal. Therefore, in an animal, it is determined whether the sympathetic nerve is active based on the number of times of the consecutive observations where the time is 67 ms or more for the R-R interval of a certain number of samples.

The control unit 330 periodically computes the time of pNNX and determines whether the sympathetic nerve is active based on the computed time of pNNX. This allows the control unit 330 to determine whether the animal on which the animal emotion estimation device 1 is mounted feels stress. The control unit 330 also estimates the emotion of the animal by Poincaré Plot analysis.

Figure 9:
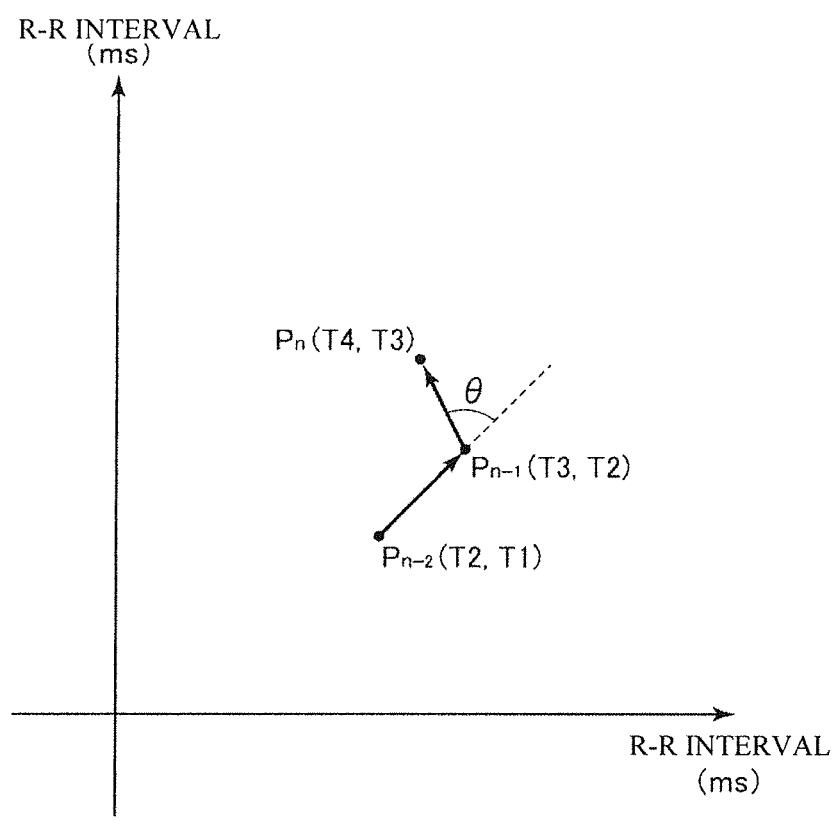
FIG. 9 is a graph illustrating an example plot of the Poincare plane.

In the Poincaré plot according to this example, as shown in FIG. 9, the time of the R-R interval is set for the X axis and the Y axis. It is assumed that the R-R interval at time t1 is set as T1, the R-R interval at time t2 is set as T2, the R-R interval at time t3 is set as T3, and the R-R interval at time t4 is set as T4 (t1<t2<t3<t4). At this time, in the Poincare plot, the points where the two consecutive R-R intervals are respectively set as the X coordinate and the Y coordinate are plotted. That is, a point $P_{n-2}$ can be plotted with the R-R interval T2 at time t2 as the X coordinate and the R-R interval T3 at time t1 as the Y coordinate. That is, the point where the new R-R interval is set as the X coordinate and the immediately preceding R-R interval is set as the Y coordinate is plotted. According to the rule, three points, i.e., the point $P_{n-2}$ (T2, T1), the point $P_{n-1}$ (T3, T2), and the point $P_n$ (T4, T3) are plotted from four consecutive R-R intervals as shown in FIG. 9. In the Poincaré Plot analysis, the control unit 330 performs an analysis based on the distance between the two points plotted as described above and the angle θ (see FIG. 9) made by the three points.

At this time, as the heart rate of the animal increases, the point to be plotted approaches the origin of the Poincare plane, and the direct distance between the two consecutive points, i.e., the distance between the points $P_{n-2}$ and $P_{n-1}$ and the distance between the points $P_{n-1}$ and $P_n$ tend to be short. The control unit 330 divides the direct distance between the two points by a certain population parameter and normalizes it to qualitatively obtain the direct distance even when the heart rate is high or low. It is preferable that the population parameter be a value that becomes relatively smaller as the heart rate becomes higher. The longer one of the sum values of the X coordinate value and the Y coordinate value of the two points is used. When the thus obtained normalized direct distance is less than the predetermined threshold value, the control unit 330 determines that the animal on which the animal emotion estimation device 1 is mounted is interested in something.

Further, the control unit 330 estimates the emotion based on the angle θ formed by two straight lines on the Poincare plane where one of the lines is formed by two consecutively plotted points and the other one of the lines is formed by a point continuous with one of the two points. That is, in the example of FIG. 9, the emotion is estimated based on the angle θ formed by a straight line connecting the point $P_{n-2}$ and the point $P_{n-1}$ and a straight line connecting the point $P_{n-1}$ and the point $P_n$.

I discovered that as the angle θ approaches 90 degrees, the animal tends to feel stress (frightened by noise, and scolded, for example). Also, I discovered that as the angle θ approaches −90 degrees, the animal tends to be more relaxed.

Accordingly, the control unit 330 computes the angle θ obtained based on the four points plotted on the Poincare plane, and determines whether stress is felt based on the angle.

If a result that is different from the result of the analysis based on the pNNX analysis is obtained, the analysis result based on the Poincaré Plot analysis is given priority for stress.

Further, the control unit 330 determines whether the heart rate around the unit time is less than or equal to a predetermined value based on the heart rate signal. If the heart rate is less than or equal to a predetermined value for a certain period of time, the control unit 330 determines that the animal feels drowsy. When determining that the animal feels drowsy, the control unit 330 determines only that the animal feels drowsy in whatever other state such as the degree of the stress or the degree of interest the animal is.

The control unit 330 estimates the emotion of the animal by performing the HRV analysis based on the heart rate signal obtained from the sensor 100 as described above.

The communication unit 340 communicates with a portable terminal such as a smartphone of the user wirelessly, and transmits the information transmitted from the control unit 330 to the portable terminal of the user according to a predetermined communication protocol. The portable terminal of the user displays the transmitted face image thereon, allowing the user to recognize the emotion of the animal by looking at the displayed face image.

The output unit 200 serves to display the face image transmitted from the control unit 330. The output unit 200 may be embodied by, for example, a plurality of LED lights provided in parallel, or may be embodied by a monitor such as a compact LCD, for example. Further, when the output unit 200 is embodied by a plurality of LED lights, the control unit 330 may designate the LED light to be lit rather than the face image.

Data

FIG. 6 is a data conceptual diagram of a face image table 600 illustrating a face image to be displayed according to the state of the animal stored in the animal emotion estimation device 1.

The face image table 600 corresponds to a table in which the state information 601 of the estimated animal and the display information 602 are associated with each other.

The state information 601 of the estimated animal corresponds to information showing the state of the animal, and includes information on the presence/absence of drowsiness, the level of the stress, and the level of interest.

The display information 602 corresponds to information showing the face image to be displayed on the output unit 200 each corresponding to the estimated state information 601 of the animal.

According to the face image table 600, the animal emotion estimation device 1 displays a drowsy face image regardless of stress or degree of interest when the animal feels drowsy (refer to the first row of the face image table 600).

Also, for example, if the animal has no drowsiness, the degree of stress is high, and the degree of interest is low, it is estimated that the animal is anxious or irritated. This displays a face image where the eyes are set as x and the mouth is set such that the animal is in a weak state (refer to the third row of the face image table 600).

The control unit 330 of the animal emotion estimation device 1 allows a memory to store the face image table 600, refers to the face image table 600 to specify the display information 602 corresponding to the estimated state of the animal, and allows the output unit 200 to display the information 602 thereon.

Operations

Figure 7:
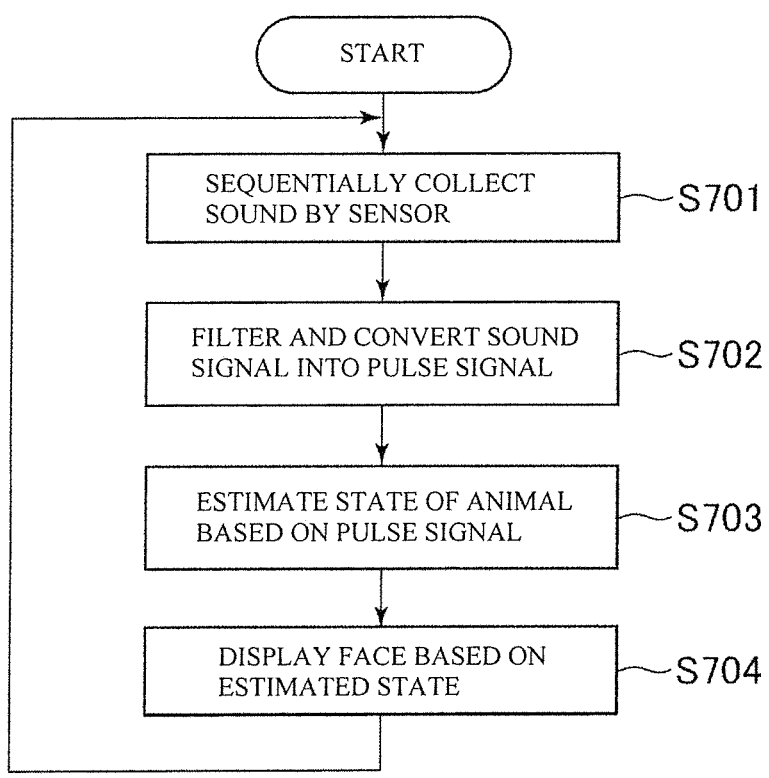
FIG. 7 is a flowchart illustrating the operations of the animal emotion estimation device.

FIG. 7 is a flowchart showing the operations of the animal emotion estimation device 1. As shown in FIG. 7, the sensor 100 of the animal emotion estimation device 1 obtains biological information of the animal (step S701). In this example, the animal emotion estimation device 1 obtains a sound signal including a heartbeat sound through the microphone 101.

The sound signal collected through the microphone 101 is transmitted to the sensor processing circuit 310. The sensor processing circuit 310 then filters and converts the sound signal into a heart rate signal (step S702). The sensor processing circuit 310 transmits the heart rate signal to the control unit 330.

The control unit 330 performs the HRV analysis to estimate the emotion of the animal based on the transmitted heart rate signal (step S703). That is, the control unit 330 determines whether the animal on which the animal emotion estimation device 1 is mounted feels drowsy, whether the animal feels stress, and whether the animal is interested in something.

The control unit 330 determines the face image corresponding to the estimated emotion using the face image table 600. The determined face image is then supplied to the output unit 200.

The output unit 200 then displays the face image specified by the control unit 330. The animal emotion estimation device 1 repeatedly executes the process shown in FIG. 7 from the time when the power is turned on until the power is turned off.

The steps correspond to the operations of the animal emotion estimation device 1.

Summary

As illustrated in the example above, the animal emotion estimation device 1 is mounted on the animal and obtains a sound signal showing the heart sound. The animal emotion estimation device 1 then specifies the heartbeat based on the sound signal, estimates the emotion of the animal based on the heartbeat, and supplies the information showing the emotion. This allows the user to recognize what emotion the animal has at a glance by looking at the supplied information. The animal emotion estimation device 1 as the sensor 100 with an outer portion covered with a sponge material maintains a close contact state with a flexibly varying skin of the animal, and efficiently and suitably obtains the heart sound.

Example 2

Unlike Example 1 above, in an animal emotion estimation device according to Example 2, the output unit 200 does not display the face image, but emits light. Depending on its luminescent color and a way of emitting light, the animal emotion estimation device expresses the estimated emotion of the animal. An animal emotion estimation device 10 according to Example 2 will be described below.

Configurations

Figure 10:
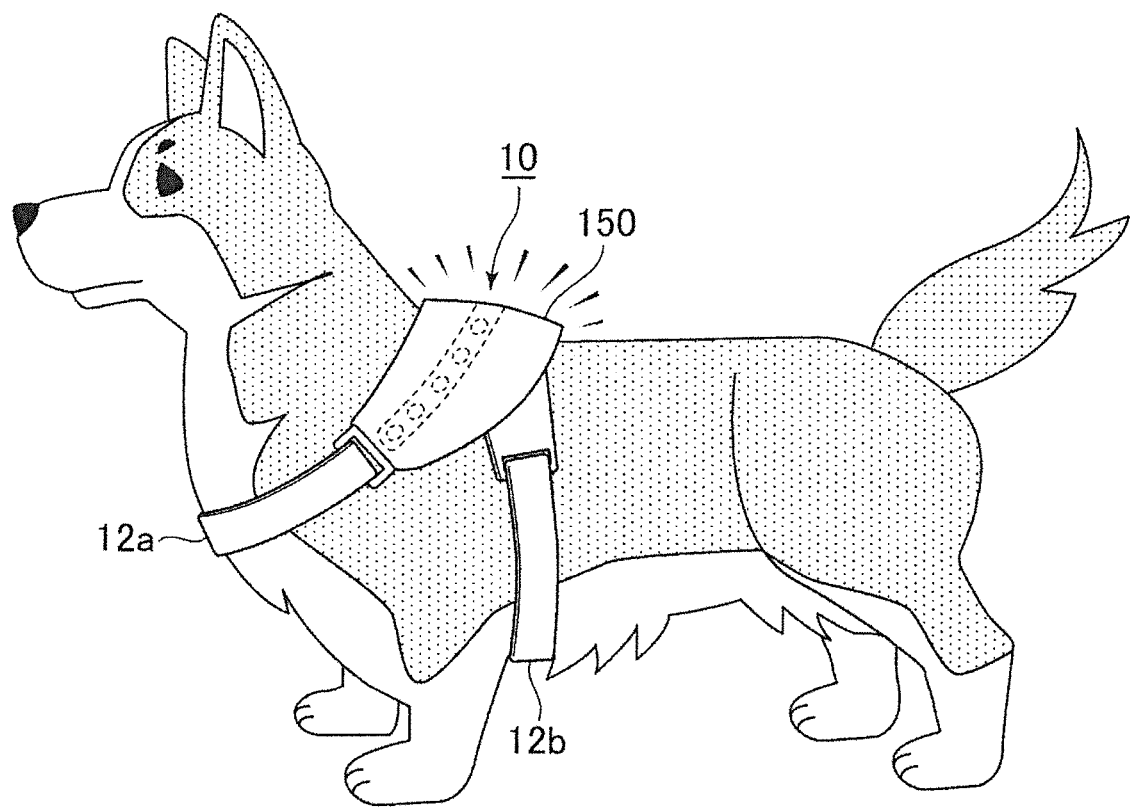
FIG. 10 is a diagram illustrating a state where an animal emotion estimation device 10 is mounted on an animal according to Example 2.
Figure 11A:
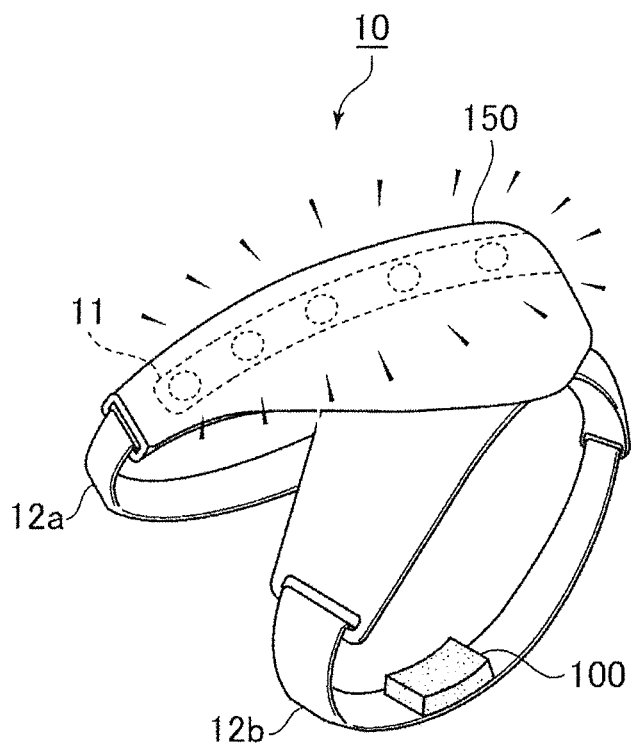
FIG. 11A is a perspective view of an external appearance of the animal emotion estimation device 10 according to Example 2.
Figure 11B:
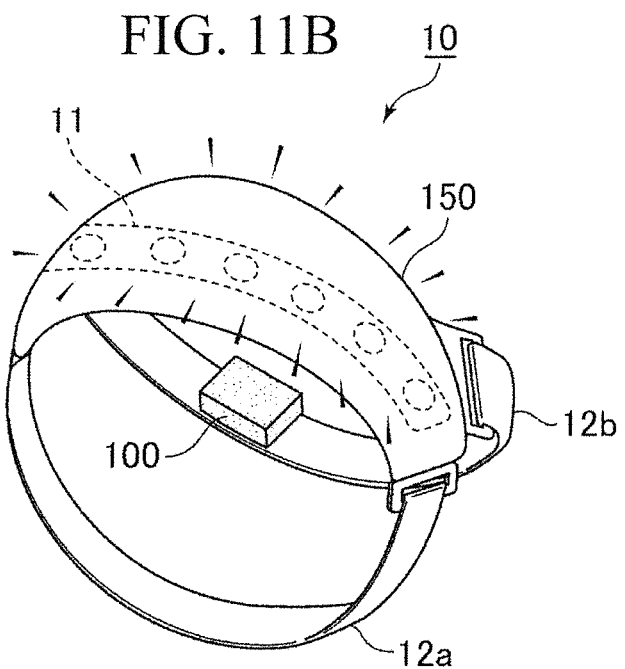
FIG. 11B is a perspective view of an external appearance of the animal emotion estimation device 10 viewed in a direction different from that in FIG. 11A.

FIG. 10 is a diagram illustrating a state in which the animal emotion estimation device 10 according to Example 2 is mounted on an animal (a dog in the example of FIG. 10). FIGS. 11A and 11B are perspective views of an external appearance of the animal emotion estimation device 10 viewed from different angles, respectively.

As shown in FIG. 10 and FIGS. 11A and 11B, the animal emotion estimation device 10 includes an output unit 1200 in place of the output unit 200 displaying the face image in the Example 1 above. The output unit 1200 is embodied by an LED tape 11 provided inside a housing 150 of the animal emotion estimation device 10. The housing 150 is made of a translucent or transparent resin that transmits light emitted from the LED tape 11 provided therein. Also, as shown in FIGS. 11A and 11B, in the animal emotion estimation device 10, belts 12a and 12b surround the chest circumference and the waist circumference of the animal as an object on which the device 10 is mounted, respectively, to prevent the device 10 from being removed from the animal on which the device 10 is mounted.

Figure 12:
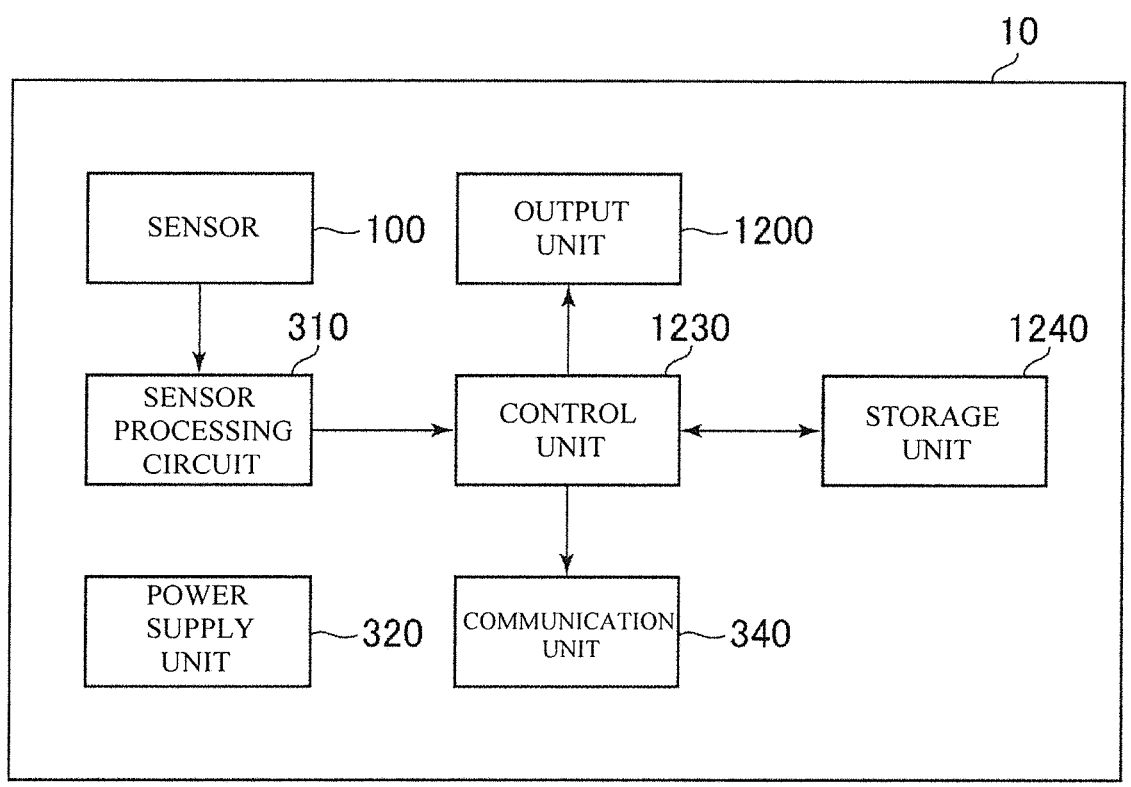
FIG. 12 is a block diagram illustrating a functional configuration of the animal emotion estimation device 10 according to Example 2.

FIG. 12 is a block diagram illustrating the functional configuration of the animal emotion estimation device 10. As shown in FIG. 12, the animal emotion estimation device 10 includes a sensor 100, a sensor processing circuit 310, a power supply unit 320, a communication unit 340, the output unit 1200, a control unit 1230, and a storage unit 1240. In Example 2, the same reference numerals are assigned to the functional portions having the same functions as those of the Example 1 above, and the description thereof is omitted.

The output unit 1200 is a light emitting medium that emits light in various colors. As described above, the output unit 1200 is embodied by the LED tape 11, for example. According to an instruction from the control unit 1230, the output unit 1200 emits light in the luminescent color and the brightness of light emission at the time point of light emission instructed. The LED tape 11 includes a plurality of LEDs in series where the luminescent color, the brightness of light emission, and the time point of light emission are controlled for each of the LEDs independently.

The control unit 1230 estimates the emotion of the animal based on the heart rate signal supplied from the sensor processing circuit 310, determines the luminescent color, the brightness of light emission, and the time point of light emission based on the estimated emotion, and transmits the determined contents to be supplied to the output unit 1200.

The control unit 1230 determines the luminescent color per unit time specified based on the heart rate signal. The control unit 1230 refers to a basic color determination table 1400 stored in the storage unit 1240, and determines a basic color in which the output unit 1200 is caused to emit light. The basic color determination table 1400 is information in which the heart rate range and the basic color that emits light when the measured heart rate is included in the heart rate range are associated with each other. The basic color determination table 1400 will be described in details below. The luminescent color is then determined such that as the heart rate is closer to the adjacent other heart rate range, the basic color of the adjacent heart rate range is mixed with the determined basic color. Also, at this time, the luminescent color is determined such that the LEDs between the LEDs that emit light in the mixed color to be mixed and the LEDs that emit light in the basic color emit light in the intermediate color to make a gradation.

The control unit 1230 estimates the emotion of the animal based on the rise and fall of the heart rate, NN50, and the Poincaré plot analysis in the same manner as in the control unit 330 illustrated in Example 1 above. The control unit 1230 specifies the activity degree of the sympathetic nerve based on the NN50 and the degree of happiness and the degree of concentration of the animal by the angle θ based on the Poincaré plot analysis.

For example, the control unit 1230 performs a normalization such that as the angle θ shown in Example 1 above is estimated to be closer to an angle at which the animal is specified as feeling happiness, i.e., as the degree of happiness that the animal feels is estimated to be higher based on the Poincaré Plot analysis, the degree of happiness of the animal is set closer to one, and as the angle θ is closer to an angle at which the animal is specified as failing to feel happiness, the degree of happiness of the animal is set closer to zero. In accordance with the numerical value (0 to 1) of the degree of happiness, the control unit 1230 then determines the degree of other colors to be mixed for the output unit 1200. The control unit 1230 determines to set the brightness higher as the degree of happiness is higher (closer to one). As for the angle θ, the angle at which the animal is specified as feeling happiness and the angle at which the animal is specified as failing to feel happiness are specified by observing the activity information of the animal and determining the way of the change of the Poincare plot at the time of the observation. That is, the angle θ in the Poincare plot at which the animal makes an action showing that the animal feels happiness may be set as an angle at which the animal feels happiness. In the same manner, the angle θ in the Poincare plot at which the animal makes an action showing that the animal fails to feel happiness may be set as an angle at which the animal fails to feel happiness.

Further, for example, the control unit 1230 specifies the relationship between i) the direct distance between the point $P_n$ and the point $P_{n-1}$ shown in Example 1 above and ii) the rise and fall of the degree of concentration based on the Poincaré Plot analysis by associating the relationship with the activity observation, and converts the rise and fall of the degree of concentration into a numerical value from 0 to 1. The control unit 1230 then determines the blinking contrast of the LED tape 11 based on the specified degree of concentration. The determination of the blinking contrast corresponds to a determination of a difference in brightness from when the brightness is gradually lowered from the highest brightness until the brightness reaches the lowest brightness or from when the brightness is gradually increased from the lowest brightness until the brightness reaches the highest brightness. That is, according to the degree of concentration, the control unit 1230 determines the highest brightness and the lowest brightness in which the LED tape 11 is caused to emit light. FIGS. 13A and 13B each illustrate an example of blinking according to the degree of concentration. FIG. 13A is a graph showing the state of the light emission control when the degree of concentration of the animal is high, and FIG. 13B is a graph showing the state of the light emission control when the degree of concentration of the animal is low. As shown in FIG. 13A, when the control unit 1230 determines that the degree of concentration of the animal is high, the control unit 1230 determines the highest brightness and the lowest brightness such that the difference between the highest brightness and the lowest brightness increases. For example, the determination is embodied such that a table in which the numerical value of the degree of concentration is associated with the highest brightness and the lowest brightness is stored in the storage unit 1240, and the control unit 1230 refers to the table. The difference La between the highest brightness L1 and the lowest brightness L2 in FIG. 13A is greater than the difference Lb between the highest brightness L3 and the lowest brightness L4 in FIG. 13B. The control unit 1230 performs a light emission control as shown in FIGS. 13A and 13B according to the degree of concentration of the animal.

The control unit 1230 transmits the luminescent color, the brightness of light emission, and the time point of light emission as determined above to the output unit 1200.

The storage unit 1240 is a storage medium that stores various programs and data needed for the operations of the animal emotion estimation device 10. The storage unit 1240 may include a hard disc drive (HDD), a solid state drive (SSD), and a flash memory, for example.

Data

FIG. 14 is a data conceptual diagram showing a data configuration example of the basic color determination table 1400 stored in the animal emotion estimation device 10.

As shown in FIG. 14, the basic color determination table 1400 corresponds to information in which a basic color 1401 and a heart rate 1402 are associated with each other.

The basic color 1401 corresponds to information defining the basic color in which the animal emotion estimation device 10 emits light, and here, may include four colors, i.e., blue, green, yellow, and red shown as an example.

The heart rate 1402 corresponds to information showing the range of the heart rate to determine the basic color in which the LED tape 11 emits light based on the heart rate measured by the sensor 100. The heart rate 1402 shows the number of times per minute here.

In the example shown in FIG. 14, the basic color blue is associated with the heart rate of 65 or less times, the basic color green is associated with the heart rate of 66 times to 70 times, the basic color yellow is associated with the heart rate of 71 times to 75 times, and the basic color red is associated with the heart rate of 76 times or more. According to the basic color determination table 1400, for example, if the heart rate measured by the sensor 100 of the animal emotion estimation device 10 is 74 times, yellow is selected as the basic color. Since the heart rate is 74 times and thus the heart rate range is close to the frequency range of the basic color red, the control unit 1230 determines to set the basic color to yellow, and mix red therewith in which the light is omitted.

Operations

FIG. 15 is a flowchart showing the operations of the animal emotion estimation device 10 according to Example 2.

The sensor 100 of the animal emotion estimation device 10 senses the heartbeat, obtains a sound signal, and supplies the sound signal to the sensor processing circuit 310. The sensor processing circuit 310 converts the obtained sound signal into a heart rate signal and transmits the heart rate signal to the control unit 1230. The control unit 1230 obtains the heart rate signal from the sensor processing circuit 310 (step S1501).

The control unit 1230 specifies the heart rate per unit time (step S1502). The control unit 1230 then refers to the basic color determination table 1400, and determines the light emission basic color in which the LED tape 11 emits light based on the specified heart rate (step S1503).

The control unit 1230 specifies predetermined LEDs of the LED tape 11 as the LEDs that are caused to emit light in basic color. Next, the control unit 1230 performs a heart rate variability analysis (HRV analysis) on the obtained heart rate signal (step S1504).

First, the control unit 1230 performs a heart rate variability analysis (HRV analysis) and specifies the degree of happiness as the emotion of the animal. The control unit 1230 then specifies the degree of mixing colors other than the basic color at the time of causing the LEDs to emit light according to the degree of happiness (step S1505). That is, the control unit 1230 controls the light emission such that the greater the degree of happiness is, the more the color unevenness is viewed, and the less the degree of happiness is, the less the color unevenness is viewed. Specifically, the storage unit 1240 stores a table in which as the degree of happiness approaches one, the number of colors other than the basic color to be mixed increases, and as the degree of happiness approaches zero, the number of colors other than the basic color decreases. This allows the control unit 1230 to refer to the table to determine the number of colors to be mixed. The control unit 1230 then determines the colors to be mixed by selecting the determined number of colors from the colors other than the basic color. At this time, the storage unit 1240 may store a table in which the colors to be mixed are determined for each basic color according to the number of colors to be mixed, and the control unit 1230 may determine the colors to be mixed using the table. Alternatively, the control unit 1230 may determine, as the color to be mixed, the color corresponding to the frequency domain adjacent to the frequency domain corresponding to the basic color in which the light is emitted in the basic color determination table 1400. The control unit 1230 causes the predetermined LEDs in the determined color to be mixed to emit light, which LEDs are the ones of the LEDs other than the LEDs caused to emit light in the basic color. As for the other LEDs, the color in which the LEDs are caused to emit light is determined such that the color gradually changes from the basic color to the color to be mixed.

Further, the control unit 1230 specifies the degree of concentration as the emotion of the animal based on the heart rate variability analysis. The control unit 1230 then determines the highest brightness and the lowest brightness in which the LEDs are caused to emit light in accordance with the degree of concentration (step S1506). The control unit 1230 determines the time point of light emission such that the contrast of light emission of the LEDs become stronger as the degree of concentration of the animal is higher.

The control unit 1230 transmits the determined luminescent color, brightness of light emission, and time point of light emission to the output unit 1200. For each LED of the LED tape 11, the output unit 1200 causes the specified LED to emit light in the transmitted luminescent color, and causes the LED to emit light to blink between the transmitted highest brightness and the lowest brightness (step S1507), and the process returns to step S1501.

The animal emotion estimation device 10 repeats this process until it receives a stop input from the user, and expresses the estimated emotion of the animal using the luminescent color and the way of emitting light.

Summary

The animal emotion estimation device 10 according to Example 2 expresses the emotion of the animal by the luminescent color of the LED, the light emission intensity (brightness), and the time point of light emission (early and late period of blinking cycle). This allows the user to easily estimate what emotion the animal has by looking at the emitted light. For example, if the device 10 relatively calmly blinks in blue or green, the device 10 presumes that the animal is calm and relaxed, and if the device 10 relatively quickly blinks in red or yellow, the device 10 presumes that the animal is excited but in concentration.

Modified Examples

Although preferred configurations are described in the examples above, the ideas according to this disclosure are not limited thereto. Various modifications included as ideas according to this disclosure will be described below.

(1) In the examples above, the communication unit 340 provided in the animal emotion estimation device 1 is an option, and if the user thinks that it is not needed to receive information on the emotion of the animal by the portable terminal such as a smartphone, the communication unit 340 may be omitted.

(2) In the examples above, the sensor 100 is set as a sound collector and configured to obtain a sound of a heartbeat. However, the sensor 100 may be other sensors as long as it obtains information that allows the emotion of the animal to be estimated. For example, the sensor 100 may be a pulse monitor, and a clinical thermometer, for example, as long as it allows the animal emotion estimation device 1 to provide information that enables the estimation of the emotion of the animal.

(3) In the examples above, as a method of expressing the emotion of the animal, a face image showing the emotion is displayed on the output unit 200, but the method is not limited to this.

Other methods may be used as long as the method allows the emotion of the animal to be provided for the user. For example, the methods may use letters and words, or may express the emotion in colors using LED lights.

For example, when the emotion is passed in letters or words, when the animal is drowsy, the emotion may be expressed such as "Sleepy . . . " or "ZZZ . . . ," and when the animal is interested in something (where the stress of the animal is low and the animal is excited), the emotion may be expressed by "What?" or "!!" In this case, the animal emotion estimation device 1 stores and uses a character information table in which character information is stored in the portion corresponding to the display information 602 of the face image table 600 in place of the face image table 600 in the example above.

Also, in expressing the emotion in color, for example, when the animal feels drowsy, the LED light may emit light in green color, and when the animal finds something interesting, the LED light may emit light in pink color. In this case, the animal emotion estimation device 1 stores and uses a color information table in which color information is stored in the portion corresponding to the image portion of the display information 602 of the face image table 600 in place of the face image table 600 in the example above.

Further, the output unit 200 may combine these to display contents to be randomly displayed at each time by selecting and displaying any of the face images, the colors, and the characters.

(4) In the examples above, the control unit 330 periodically computes the pNNX time. This may be embodied by a method in which the average value of the heartbeat of the animal on which the device is mounted is obtained in advance and an appropriate value is stored in the memory of the control unit 330. In this case, since the pNNX is not needed to be computed every time, reducing the processing loads on the control unit 330.

(5) In the examples above, one microphone 101 is provided for the sensor 100 and is illustrated. However, the number of the microphones is not limited to one. The animal emotion estimation device 1 may include two or more microphones configured to obtain a sound including the heartbeat sound more efficiently.

Figure 8A:
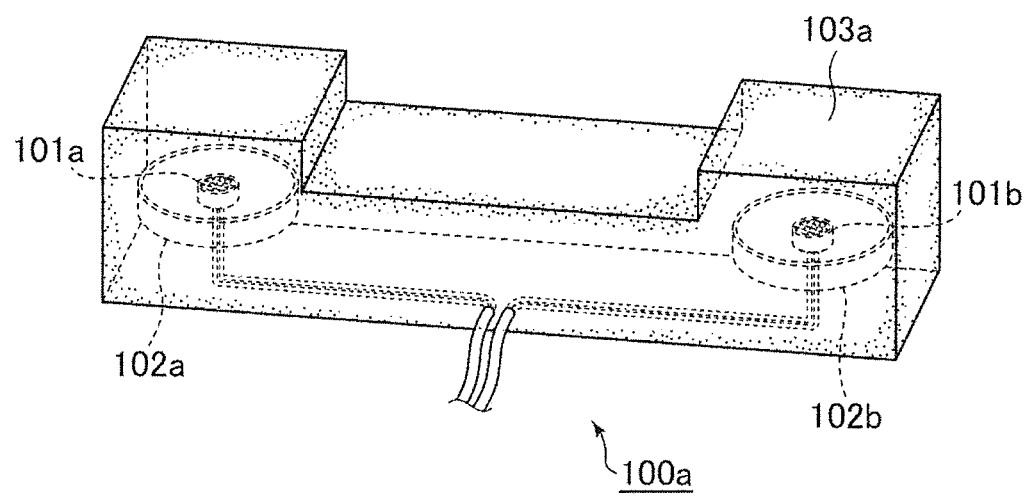
FIG. 8 is a diagram illustrating another configuration example of the sensor 100.
Figure 8B:
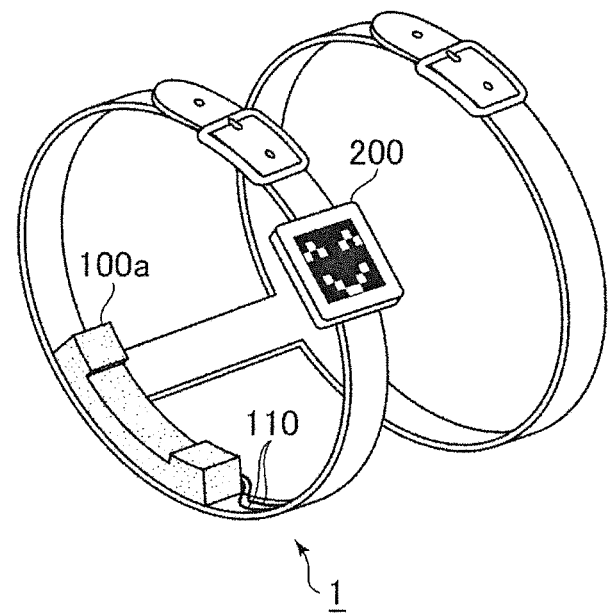

FIG. 8 shows one example thereof. As shown in FIG. 8A, a sensor 100a includes, at one end of an inner portion of a U-shaped sponge 103a, a basal portion 102a and a microphone 101a on a bottom portion of the basal portion 102a, and at the other end, a basal portion 102b and a microphone 101b on a bottom portion of the basal portion 102b. The configuration of the basal portions and the microphones is the same as that shown in Example 1 above. As shown in FIG. 8B, the sensor 100a is provided on a harness of the animal emotion estimation device 1.

Even if one of the microphones cannot collect sounds since it is apart from the skin of the animal due to some reasons, the configuration allows the other one of the microphones to collect sounds. This increases the probability of allowing the emotion of the animal to be estimated without interruption to increases the reliability as a device.

Although FIG. 8 shows the case where two microphones are provided, the number of microphones may be three. In this case, the sponge 103a may be T-shaped and a further microphone may be arranged at the other end portion thereof. Alternatively, the sponge 103a may be cross-shaped to provide further microphones at the other end portion or the center portion thereof.

When multiple microphones are used, the animal emotion estimation device 1 may employ a configuration using the synthesized wave of the sound signal supplied from each microphone as a sound signal, or a configuration selecting and using a sound signal clearly obtained through the microphones.

Although FIG. 8A shows the U-shaped sponge 103a, the sponge 103a may be a rectangular parallelepiped.

(6) As for the sponge 103 in the examples above, a material other than sponge may be used as long as it can maintain the close contact state with the skin of the animal on which the animal emotion estimation device 1 is mounted even if the animal moves. Other materials may be used as long as they are materials having flexibility and sound propagating properties.

(7) In the examples above, the example in which the number of seconds of the pNNX analysis is computed as 6.7% of the R-R interval is shown. However, a numerical value other than 6.7% may be used. Depending on the animal on which the device is mounted, the device may be used by setting an appropriate value.

(8) In the examples above, the HRV analysis based on the time domain analysis such as NN50 is performed. However, a discrete Fourier Transform (Fast Fourier Transform) may be performed on the sensed heart rate signal, and analysis in the frequency domain may be performed to estimate the emotion of the animal. Specifically, the variance between the heartbeats is subjected to a Fourier transform, and the degree of activity of the sympathetic nerve system is specified according to the distribution of the high frequency component and the low frequency component. As described above, the animal emotion estimation devices 1, 10 may estimate the emotion of the animal based on the analysis in the frequency domain.

(9) In Example 2 above, although not specifically described, the animal emotion estimation device 10 may transmit the luminescent color, the brightness of light emission, and the time point of light emission determined based on the estimated emotion of the animal to an external light emitting device to allow the device to emit light. For example, a configuration may be employed in which a blade of a toy imitating a sword including LEDs therein is caused to emit light. Alternatively, a configuration may be employed in which LEDs are provided in the eyes of a toy imitating an animal so that the LEDs are caused to emit light. Also, a sensor is mounted on a pet/livestock toilet and the excretion time is recorded so that the heart rate at the time of excretion is recorded as a target to help to predict symptoms such as urinary concrement and cystitis, for example. Specifically, the heart rate analysis of the heart rate signal at the time when the sensor is reacting is performed to specify whether the animal is suffering at the time when the animal excretes, allowing the possibility of the diseases such as urinary concrement and cystitis to be predicted. To achieve this, the animal emotion estimation device 10 may receive a signal from the sensor mounted on the pet/livestock toilet, and give identification information to the heart rate signal at that time, which identification information identifies the heart rate signal as a heart rate signal of the animal at the time when the animal is at the pet/livestock toilet. This allows the animal emotion estimation device 10 to specify in what state the heart rate analysis is performed. Also, when the analysis result based on the heart rate signal and the heartbeat signal is supplied to the outside, the identification information thereof may be supplied to be used for the emotional analysis of the animal by the user.

(10) In the examples above, the animal emotion estimation devices 1, 10 estimate the emotion of the animal. However, the animal emotion estimation devices 1, 10 may be configured such that the communication unit 340 transmits the sensed heart rate signal to an external device (for example, a portable terminal of the user), the external device estimates the emotion of the animal, determines the information to be supplied by the output units 200, 1200, and transmits the determined face image and luminescent color to the animal emotion estimation device 10, and the output units 200, 1200 of the animal emotion estimation devices 1, 10 supply the received face image and luminescent color.

(11) In Example 2 above, the example using the LED tape 11 that emits light according to a form of the output unit 1200 is described. However, the light emitting means is not limited to the LED tape. For example, the output unit 1200 may be embodied by a plurality of LEDs individually capable of controlling luminescent color, or by other lamps.

(12) In Example 2 above, although not specifically described, the animal emotion estimation device 10 may be provided such that when the device 10 is mounted on the animal, the light emitting surface of each LED used for light emission faces the inner side of the device, i.e., is oriented in the direction toward the animal. This is because if the LED is caused to emit light directly to the outside, in some cases, the light emission is too strong, and thus there is a possibility that the image may be blown out when the animal is photographed with a camera, for example. However, such a possibility can be limited by employing a configuration in which the light emitting surface of the LED is disposed facing the inner side of the device.

Figure 16A:
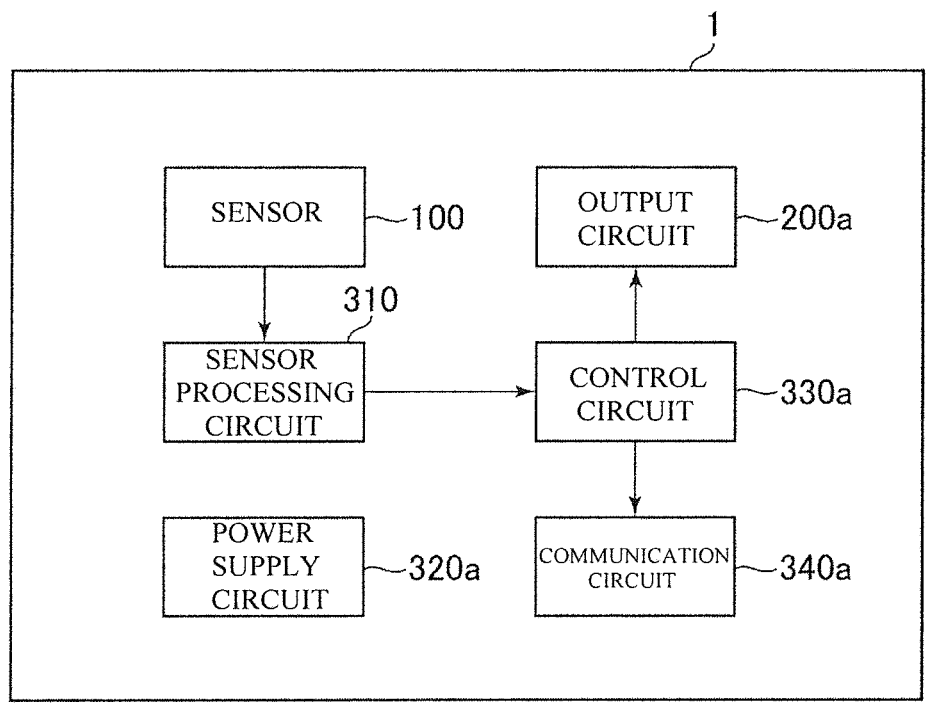
FIG. 16A is a block diagram illustrating a functional configuration of the animal emotion estimation device 1.
Figure 16B:
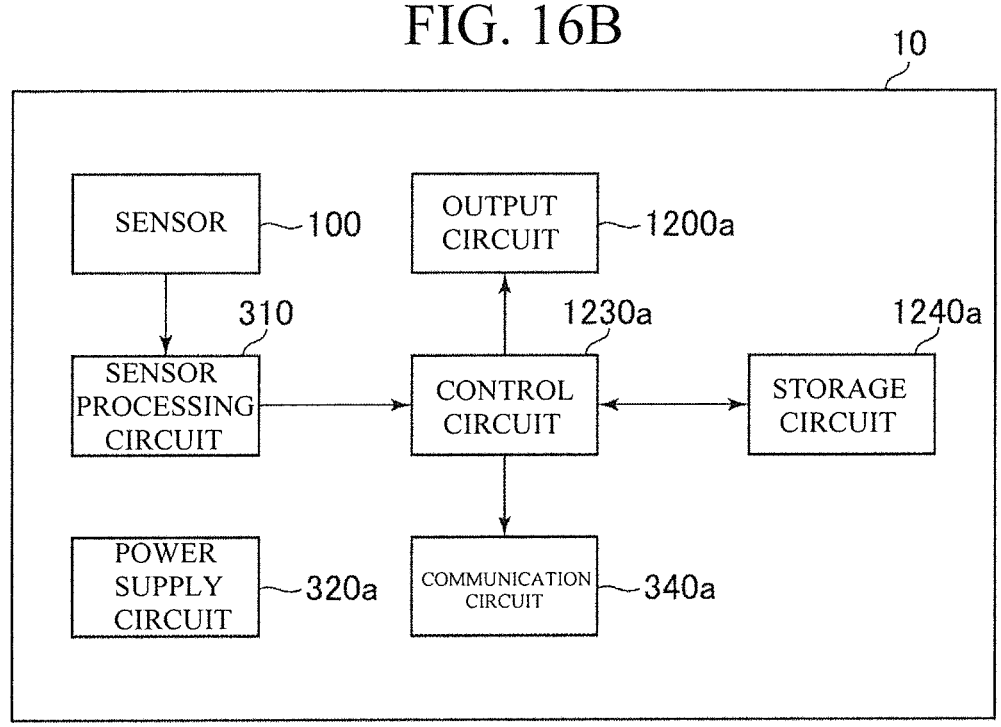
FIG. 16B is a block diagram illustrating a functional configuration of the animal emotion estimation device 10.

(13) Each functional part of the animal emotion estimation devices 1, 10 is embodied by a logical circuit (hardware) or a dedicated circuit formed in an integrated circuit (IC) chip or a large scale integration (LSI), or the devices may be embodied by software using a central processing unit (CPU) and a memory. Further, each functional part may be embodied by one or a plurality of integrated circuits, and the functions of the functional units may be embodied by a single integrated circuit. The LSI may be sometimes referred to as VLSI, super LSI, and ultra LSI, for example, depending on the difference of degree of integration. That is, for example, as shown in FIG. 16A, the animal emotion estimation device 1 may be configured to include a sensor 100, a sensor processing circuit 310, a power supply circuit 320a, an output circuit 200a, a control circuit 330a, and a communication circuit 340a. In the same manner, as shown in FIG. 16B, the animal emotion estimation device 10 may be configured to include a sensor 100, a sensor processing circuit 310, a power supply circuit 320a, an output circuit 1200a, a control circuit 1230a, a communication circuit 340a, and a storage circuit 1240a. Each circuit has the same function as each functional part having the same name shown in the examples above.

When each functional part of the animal emotion estimation devices 1, 10 is embodied by the software, the devices may include a CPU that executes the instructions of the animal emotion estimation program that embodies each function, a read only memory (ROM) or a storage device (hereinafter they are referred to as recording medium) that stores the animal emotion estimation program and various data recorded to be readable by a computer (or CPU), and a random access memory (RAM) that develops the animal emotion estimation program. The computer (or the CPU) then reads and executes the animal emotion estimation program from the recording medium, achieving the object of the present disclosure. As the recording medium, a non-transitory tangible medium such as a tape, a disk, a card, a semiconductor memory, and a programmable logical circuit may be used, for example. Also, the animal emotion estimation program may be supplied to the computer via any transmission medium (communication network and broadcast wave, for example) that transmits the animal emotion estimation program. The present disclosure may also be embodied in the form of a data signal embedded in a carrier wave where the animal emotion estimation program is embodied through the electronic transmission.

The animal emotion estimation program may be implemented by a programming language such as C language and C++, a script language such as ActionScript, JavaScript (registered trademark), an object-oriented programming language such as Objective-C, Java (registered trademark), and a markup language such as HTML5.

(14) Although this disclosure has been described with reference to drawings and examples, it should be noted that those skilled in the art can easily make various deformations and modifications based on the disclosure. Accordingly, it should be noted that these deformations and modifications are included in the scope of the disclosure. For example, the functions included in the means and the steps, for example, are rearrangeable as long as the functions are logically consistent with each other, and a plurality of means and steps may be combined together or divided. For example, the light emission control shown in the examples above is an example, and the correspondence relationship of light emission controls performed based on the heart rate and the heart rate analysis (correspondence relationship among the determination of basic color, the determination of color unevenness, and the determination of brightness of light emission) may be suitably changed, and further, the blinking cycle of light emission may be changed.

(15) The configurations shown in the examples described above and the various modified examples may be appropriately combined.

Supplement

The sound collector, the animal emotion estimation device, and the animal emotion estimation method according to one example, and the advantages achieved from the example will be described.

(A) A sound collector according to an example includes: an elastic member having a recess; a sound concentrating microphone provided on the bottom portion of the recess; and an impact absorber that covers the entire of the elastic member and the sound concentrating microphone.

Accordingly, the sound collector includes the impact absorber, allowing the sound collector to maintain a close contact state with the animal, and the sound concentrating microphone is provided on the bottom portion of the elastic member having the recess, allowing the microphone to efficiently collect a sound in the direction where the recess is directed.

Also, the animal emotion estimation device according to an example includes the sound collector, a harness for mounting the sound collector on an animal, a converter that filters and converts a sound collected through the sound collector into a heart rate signal, an estimation portion that estimates an emotion of the animal based on the heart rate signal, and an output unit that supplies information showing the emotion estimated by the estimation portion.

An animal emotion estimation method according to an example corresponds to an animal emotion estimation method of estimating an emotion of an animal by an animal emotion estimation device mounted on an animal, where the method includes the steps of: obtaining a sound signal including a heart sound of the animal, converting the obtained sound signal into a heart rate signal, estimating an emotion of the animal based on the heart rate signal, and supplying information showing the estimated emotion.

Accordingly, the animal emotion estimation device estimates the emotion of the animal based on the heart rate signal of the animal, and supplies information showing the estimated emotion. This allows the user to recognize what emotion the animal has at a glance.

(B) In the sound collector according to (A) above, the recess may be formed in a parabolic shape.

The recess is shaped in a parabolic shape, allowing the sound collector to efficiently collect a sound in the direction in which the recess is directed.

(C) In the sound collector according to (A) or (B) above, the impact absorber may be a sponge.

Accordingly, the sponge covers the circumference of the sound concentrating microphone, and the flexibility of the sponge allows the sound collector to maintain the close contact state with the target of sound collection.

(D) In the animal emotion estimation device according to (A) above, the output unit may be an LED light showing the emotion of the animal by the lit color. Accordingly, the device expresses the emotion of the animal in color. This allows the user to recognize the mood of the animal to some extent and easily communicate with the animal. For example, the light is lit in red when the animal is angry, and the light is lit in green when the animal is relaxed or sleepy. Accordingly, the animal emotion estimation device allows the user to recognize the emotion of the animal.

(E) In the animal emotion estimation device according to (A) above, the output unit may be a display device for displaying a face image showing the emotion of the animal.

Accordingly, the animal emotion estimation device allows the user to recognize the emotion of the animal at a glance.

(F) In the animal emotion estimation device according to any one of (A), (D), and (E) above, the estimation portion may estimate the degree of interest and the degree of stress of the animal based on the heart rate signal to estimate the emotion of the animal based on the degree of stress and the degree of interest.

This allows the animal emotion estimation device to estimate the degree of stress and the degree of interest of the animal based on the heart rate signal of the animal. This in turn allows the animal emotion estimation device to estimate the emotion of the animal based on the estimated degree of stress and the degree of interest.

(G) In the animal emotion estimation device according to any one of the (A) and (D) to (F) above, the estimation portion may specify a first heart rate time T1 between the first beat and the second beat continuous to the first beat, a second heart rate time T2 between the second beat and the third beat continuous to the second beat, and a third heart rate time T3 between the third beat and the fourth beat continuous to the third beat based on the heart rate signal, and estimate the degree of interest of the animal based on the distance between the point $P_n$ (T2, T1) and the point $P_{n+1}$ (T3, T2) when the points $P_n$ and $P_{n+1}$ are plotted on the coordinate system in which the heart beat time is set for each of the horizontal axis and the vertical axis.

This allows the animal emotion estimation device to estimate the degree of interest of the animal according to the change of the beat interval of the heart rate signal.

(H) In the animal emotion estimation device according to any one of the (A) and (D) to (G) above, the estimation portion may specify a fourth heart rate time T4 between the fourth beat and the fifth beat continuous to the fourth beat, and estimate the degree of stress of the animal based on the angle formed by a straight line obtained by connecting the point $P_n$ and the point $P_{n+1}$ and a straight line obtained by connecting the point $P_{n+1}$ and the point $P_{n+2}$ (T4, T3).

This allows the animal emotion estimation device to estimate the degree of stress of the animal according to the change of the beat interval of the heart rate signal. This in turn allows the animal emotion estimation device to determine pleasure and discomfort of the animal based on the degree of stress.

(I) In the animal emotion estimation device according to the (D) above, the estimation portion may specify the heart rate per unit time based on the heart rate signal and determine the color in which the LEDs are caused to emit light based on the specified heart rate.

This allows the animal emotion estimation device to emit light in a color showing the emotion of the animal based on the heart rate that contributes to the estimation of the emotion, allowing the user to easily estimate the emotion of the animal based on the luminescent color in which the animal emotion estimation device emits light.

(J) In the animal emotion estimation device according to the (I) above, the animal emotion estimation device may include a storage unit that associates and stores a basic color in which the LED is caused to emit light with the range of the heart rate per unit time, and the estimation portion may specify the basic color corresponding to the specified heart rate per unit time and determine the color in which the LED is caused to emit light based on the heart rate signal.

The color in which the LED is caused to emit light is associated with the heart rate range and stored, allowing the animal emotion estimation device to determine the basic color in which the LED is caused to emit light.

(K) In the animal emotion estimation device according to the (J) above, the output unit may include a plurality of LED lights, the estimation portion may specify basic color LEDs caused to emit light in basic color among the LEDs, and the LEDs other than the basic color LEDs may be caused to emit light in color associated with a range of the heart rate adjacent to the range of the heart rate specified based on the heart rate signal where the heart rate of the associated range is closer to the heart rate specified based on the heart rate signal.

This allows the animal emotion estimation device to have variations based on the luminescent color in which the LEDs are caused to emit light to express various emotions by various light emission methods. This allows the device to cause the light to emit light such that the user is also allowed to recognize the light as fun and interesting as an appearance.

(L) In the animal emotion estimation device according to the (K) above, the estimation portion may estimate the degree of happiness of the animal based on the heart rate signal and specify the color unevenness when the LED is caused to emit light based on the estimated degree of happiness.

This allows the animal emotion estimation device to mix various colors according to the degree of happiness of the animal such that the LEDs are caused to emit light in various colors or in the limited number of colors to be mixed, allowing the user to specify the degree of happiness of the animal at a glance.

(M) In the animal emotion estimation device according to the (L) above, the estimation portion may estimate the degree of concentration of the animal based on the heart rate signal, and specify the highest brightness and lowest brightness in which the LEDs are caused to blink based on the estimated degree of concentration.

This allows the animal emotion estimation device to express the degree of concentration of the animal in the blinking interval of the light emission, allowing the user to recognize the degree of concentration of the animal with respect to the matters at a glance. For example, if the intensity difference of blinking is strong, the user is allowed to recognize that the animal is strongly interested in certain events. In contrast, if the intensity difference of blinking is weak, for example, the user is allowed to recognize that the animal is in a calm state.

What is claimed is:

1. A sound collector comprising:
an elastic member having a recess,
a sound concentrating microphone provided on a bottom portion of the recess, the sound concentrating microphone outputting a sound signal,
an impact absorber that entirely covers the elastic member and the sound concentrating microphone, and
a converter that converts the sound signal into a heart rate signal, wherein
the converter includes:
a high-pass filter that removes a low frequency component from the sound signal to output a high-frequency signal,
an operation amplifier having an inverse input terminal, a non-inverse input terminal, and an output terminal, and
a band-pass filter provided between the non-inverse input terminal and the output terminal, wherein
the inverse input terminal is connected to the output of the high-pass filter,
the non-inverse input terminal does not receive any signal other them the signal from the band-pass filter,
the output terminal outputs an amplified high-frequency signal having a predetermined frequency, and
the band-pass filter passes a part of the amplified high-frequency signal from the output terminal to the non-inverse input terminal.

2. The sound collector according to claim 1, wherein the recess is formed in a parabolic shape.

3. The sound collector according to claim 1, wherein the impact absorber is a sponge.

4. An animal emotion estimation device comprising:
the sound collector according to claim 1;
a harness that mounts the sound collector on an animal;
an estimation portion that estimates an emotion of the animal based on the heart rate signal; and
an output unit that supplies information showing the emotion estimated by the estimation portion.

5. The animal emotion estimation device according to claim 4, wherein the output unit is an LED light that shows the emotion of the animal in a lit color.

6. The animal emotion estimation device according to claim 4, wherein the output unit is a display unit that displays a face image showing the emotion of the animal.

7. The animal emotion estimation device according to claim 4, wherein the estimation portion estimates a degree of interest and a degree of stress of the animal based on the heart rate signal and estimates the emotion of the animal based on the degree of interest and the degree of stress.

8. The animal emotion estimation device according to claim 5, wherein the estimation portion specifies a heart rate per unit time based on the heart rate signal and determines a color in which the LED is caused to emit light based on the identified heart rate.

9. The animal emotion estimation device according to claim 8, further comprising a storage unit that associates and stores a basic color in which the LED is caused to emit light with a range of the heart rate per unit time, and the estimation portion specifies the basic color corresponding to the specified heart rate per unit time and determines a color in which the LED is caused to emit light based on the heart rate signal.

10. The animal emotion estimation device according to claim 9, wherein the output unit includes a plurality of LEDs, the estimation portion specifies a basic color LED caused to emit light in the basic color among the LEDs, and the LEDs other than the basic color LED are caused to emit light in color associated with a range of the heart rate adjacent to a range of the heart rate specified based on the heart rate signal where the heart rate of the associated range is closer to the heart rate specified based on the heart rate signal.

11. The animal emotion estimation device according to claim 8, wherein the estimation portion estimates a degree of happiness of the animal based on the heart rate signal and specifies a color unevenness when the LED is caused to emit light based on the estimated degree of happiness.

12. The animal emotion estimation device according to claim 8, wherein the estimation portion estimates a degree of concentration of the animal based on the heart rate signal, and specifies a highest brightness and a lowest brightness in which the LEDs are caused to blink based on the estimated degree of concentration.

13. The animal emotion estimation device according to claim 9, wherein the estimation portion estimates a degree of happiness of the animal based on the heart rate signal and specifies a color unevenness when the LED is caused to emit light based on the estimated degree of happiness.

14. The animal emotion estimation device according to claim 9, wherein the estimation portion estimates a degree of concentration of the animal based on the heart rate signal, and specifies a highest brightness and a lowest brightness in which the LEDs are caused to blink based on the estimated degree of concentration.

15. The animal emotion estimation device according to claim 10, wherein the estimation portion estimates a degree of concentration of the animal based on the heart rate signal, and specifies a highest brightness and a lowest brightness in which the LEDs are caused to blink based on the estimated degree of concentration.

16. The sound collector according to claim 1, wherein the band-pass filter includes:
a first resistor connected between the output terminal and the non-inverse input terminal;
a capacitor connected between the output terminal and the non-inverse input terminal in parallel with the first resistor; and
a second resistor connected between the non-inverse input terminal and ground.

17. An animal emotion estimation device, comprising:
an elastic member having a recess,
a sound concentrating microphone provided on a bottom portion of the recess,
an impact absorber that entirely covers the elastic member and the sound concentrating microphone,
a harness that mounts the sound collector on an animal;
an estimation portion that estimates an emotion of the animal based on the heart rate signal; and
an output unit that supplies information showing the emotion estimated by the estimation portion, wherein
the estimation portion estimates a degree of interest and a degree of stress of the animal based on the heart rate signal and estimates the emotion of the animal based on the degree of interest and the degree of stress, and
the estimation portion specifies a first heart rate time T1 between a first beat and a second beat continuous to the first beat, a second heart rate time T2 between the second beat and a third beat continuous to the second beat, and a third heart rate time T3 between the third beat and a fourth beat continuous to the third beat based on the heart rate signal, and estimates the degree of interest of the animal based on a distance between a point $P_n$ (T2, T1) and a point $P_{n+1}$ (T3, T2) when the points $P_n$ and $P_{n+1}$ are plotted on a coordinate system in which a heartbeat time is set for each of a horizontal axis and a vertical axis.

18. The animal emotion estimation device according to claim 17, wherein the estimation portion specifies a fourth heart rate time T4 between the fourth beat and a fifth beat continuous to the fourth beat, and estimates the degree of stress of the animal based on an angle formed by a straight line obtained by connecting the point $P_n$ and the point $P_{n+1}$ and a straight line obtained by connecting the point $P_{n+1}$ and a point $P_{n+2}$ (T4, T3).

19. An animal emotion estimation method of estimating an emotion of an animal by an animal emotion estimation device mounted on an animal, the method comprising:
   obtaining a sound signal including a heart sound of the animal;
   converting the obtained sound signal into a heart rate signal;
   estimating an emotion of the animal based on the heart rate signal; and
   supplying information showing the estimated emotion, wherein
   the estimating estimates a degree of interest and a degree of stress of the animal based on the heart rate signal and estimates the emotion of the animal based on the degree of interest and the degree of stress, and
   the estimating specifies a first heart rate time T1 between a first beat and a second beat continuous to the first beat, a second heart rate time T2 between the second beat and a third beat continuous to the second beat, and a third heart rate time T3 between the third beat and a fourth beat continuous to the third beat based on the heart rate signal, and estimates the degree of interest of the animal based on a distance between a point $P_n$ (T2, T1) and a point $P_{n+1}$ (T3, T2) when the points $P_n$ and $P_{n+1}$ are plotted on a coordinate system in which a heartbeat time is set for each of a horizontal axis and a vertical axis.

* * * * *